United States Patent [19]
Rossano et al.

[11] Patent Number: 5,710,286
[45] Date of Patent: Jan. 20, 1998

[54] PROCESSES AND INTERMEDIATES FOR THE PREPARATION OF CYCLIC UREA HIV PROTEASE INHIBITORS

[75] Inventors: Lucius Thomas Rossano, Newark; Young Sek Lo, Hockessin, both of Del.

[73] Assignee: The DuPont Merck Pharmaceutical Company, Wilmington, Del.

[21] Appl. No.: 557,254

[22] Filed: Nov. 14, 1995

Related U.S. Application Data

[62] Division of Ser. No. 268,702, Jun. 30, 1994, Pat. No. 5,466,797.
[51] Int. Cl.$^6$ ................................................ C07D 325/00
[52] U.S. Cl. .............................. 549/352; 540/502; 540/503
[58] Field of Search .................................. 540/502, 503; 549/352

[56] References Cited

U.S. PATENT DOCUMENTS

| | | | |
|---|---|---|---|
| 5,532,356 | 7/1996 | Smyser et al. | 540/492 |
| 5,532,357 | 7/1996 | Rodgers et al. | 540/492 |

*Primary Examiner*—Yogendra N. Gupta

[57] ABSTRACT

This invention relates to novel compounds and derivatives thereof containing a trioxepane protected diol in addition to a hydrazone, hydrazine, amine, or cyclic urea moiety; methods for the preparation of said compounds; and the use of said compounds in processes to prepare human immunodeficiency virus (HIV) protease inhibitors which effectively inhibit HIV. The novel compounds provided by this invention have the formulae:

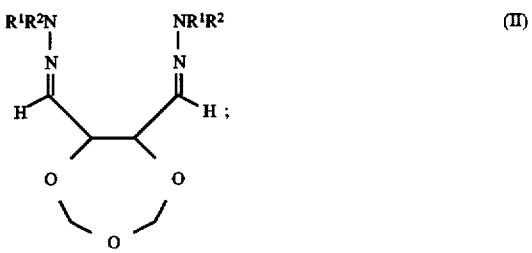

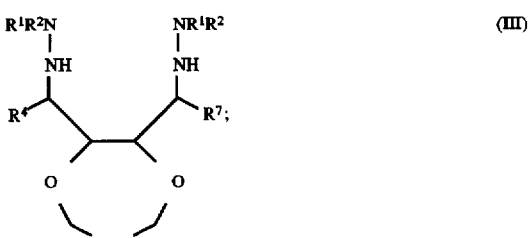

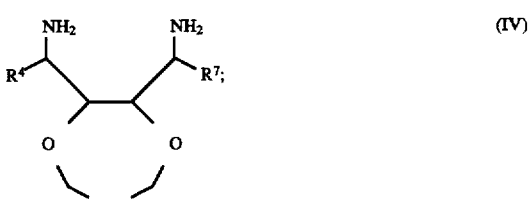

and

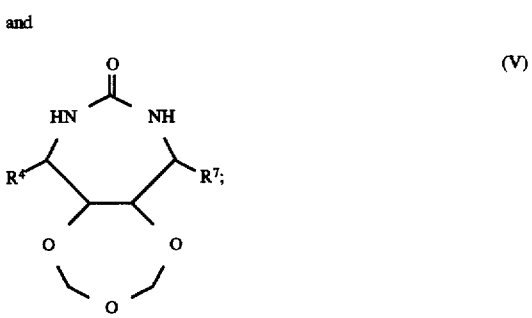

wherein the substituents are as defined herein.

4 Claims, No Drawings

PROCESSES AND INTERMEDIATES FOR THE PREPARATION OF CYCLIC UREA HIV PROTEASE INHIBITORS

This is a division of application Ser. No. 08/268,702, filed Jun. 30, 1994 now U.S. Pat. No. 5,466,797.

FIELD OF THE INVENTION

This invention relates to novel compounds and derivatives thereof containing a trioxepane protected diol in addition to a hydrazone, hydrazine, amine, or cyclic urea moiety; methods for the preparation of said compounds; and the use of said compounds in processes to prepare human immunodeficiency virus (HIV) protease inhibitors which effectively inhibit HIV.

BACKGROUND OF THE INVENTION

Many nonpeptide, C-2 symmetric and pseudosymmetric compounds have shown good biological activity as HIV protease inhibitors. Compounds and methods for their preparation are increasingly found in the literature: (Kempf, D. et al., *J. Org. Chem.* 57 5692–5700 (1992); Livermore, D. et al., *J Med Chem,* 36 3784–3794 (1993); Lam, P., et al., *Science* 263 380–384 (1994); European Patent EP 402,646; Dreyer et al., *Biochemistry* 32(3) 937–47 (1993); Jadhav et al, *Bioorganic & Med. Chem. Lett* 2(4) 353–356 (1992); Jadhav et al., U.S. Pat. No. 5,294,720, issued Mar. 15, 1994).

Seebach has demonstrated that the seven membered ring acetal, trioxepane, is a useful protecting group for tartaric acid (Seebach, D. et al., *Chimia,* 45 (7/8) 238–244 (1991)).

Baker and Condon, *J. Org. Chem.* 58, 3277–3284 (1993), disclose a method for the preparation of linear diaminodiols from (−)-2,3-O-isopropylidene-D-threitol. Cyclization of the linear diol is not taught.

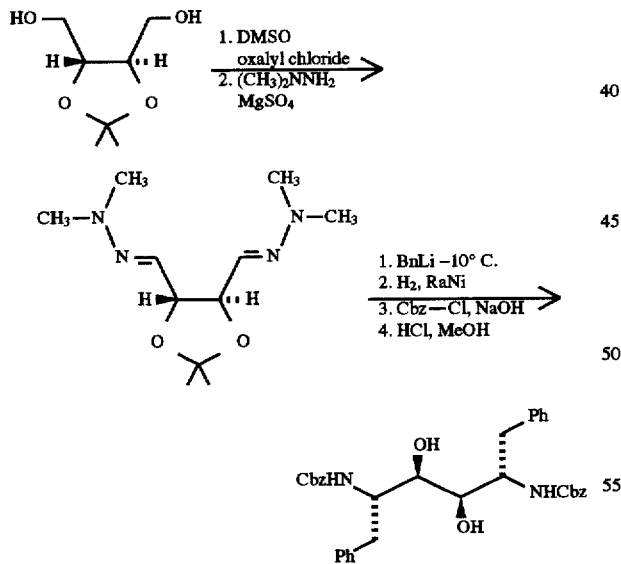

Copending commonly assigned patent application U.S. Ser. No. 08/047,330, filed Apr. 15, 1993, discloses a process for the synthesis of cyclic ureas, as shown below, wherein at least one of $R^{22}$ and $R^{23}$ are hydrogen, useful as HIV-1 protease inhibitors. The analogous groups $R^5$, $R^{5a}$ and $R^6$, $R^{6a}$ can be taken together to form a ketal ring. As well they can be taken separately and can be 2-methoxyethoxymethyl ether (MEM), methoxymethyl ether (MOM), triethylsilyl (TES), or 2-(trimethylsilyl)ethoxymethyl (SEM) protected hydroxyls.

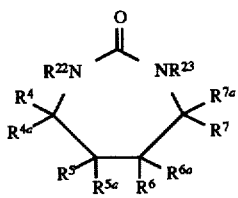

The claimed process comprises contacting a compound of the formula:

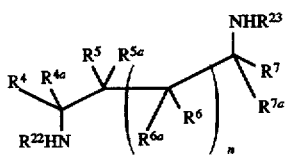

with a suitable cyclizing reagent in a suitable solvent, said solvent optionally containing a base, thereby to form the cyclic compound. The hydroxyl protecting groups taught in that process are less advantageous than the trioxepane protecting group of the present invention.

Acetonide has been used to protect the diol function in the preparation of linear HIV protease inhibitors (Baker, W. et al., *J. Org. Chem.* 58, 3277–3284 (1993); Baker, W. et al., *Tetrahedron Lett.* 33, 1581–1584 (1992)).

Each method described above utilizes expensive amino acid or saccharide as a source of chiral starting materials. Each method described above requires chromatographic purification of the products. The expense of the starting materials and the requirement of performing chromatography to purify reaction products renders the above-described methods undesirable for large scale production of HIV protease inhibitors.

There is a need for an efficient method for the preparation of HIV protease inhibitors that uses inexpensive chiral starting materials such as tartaric acid, and which does not require chromatography.

SUMMARY OF THE INVENTION

This invention provides novel compounds of the formulae (II), (III), (IV), and (V) and novel methods for their preparation from a compound of the formula:

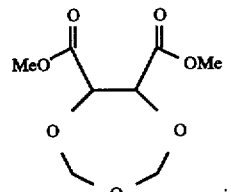

The novel methods provided by the present invention provide high yields, can be conducted on a multikilogram scale, and eliminate the need for chromatographic purification of intermediates and final product. Compounds of the formula (I)–(V) are useful as intermediates for the preparation of HIV protease inhibitor agents.

DETAILED DESCRIPTION OF THE INVENTION

The present invention provides processes and intermediates useful for the preparation of cyclic HIV protease inhibitors. Such cyclic HIV protease inhibitors are disclosed in copending commonly assigned U.S. patent application Ser. No. 08/197,630, Lam et al., filed Feb. 16, 1994 and Lam et al., PCT International Publication Number WO 93/07,128, the disclosures of which are incorporated herein by reference. Such cyclic HIV protease inhibitors are useful for the inhibition of HIV and the treatment of HIV infection. Such cyclic HIV protease inhibitors are also useful for the inhibition of HIV in an ex vivo sample containing HIV or expected to be exposed to HIV. Thus, such cyclic HIV protease inhibitors may be used to inhibit HIV present in a body fluid sample (for example, a serum or semen sample) which contains or is suspected to contain or be exposed to HIV. Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

[1] This invention provides novel trioxepane protected diol compounds of the formula

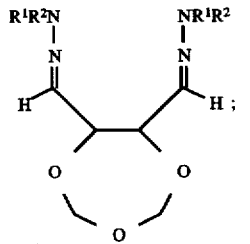
(II)

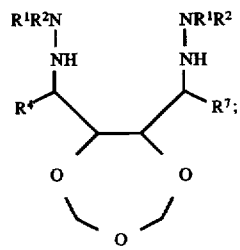
(III)

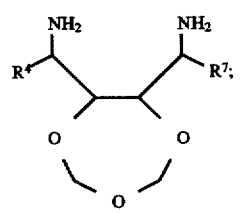
(IV)

and

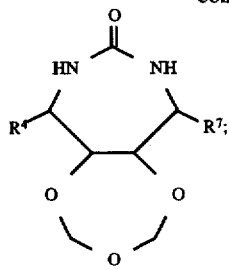
(V)

wherein:

$R^1$ and $R^2$ are independently selected from the group: $C_1$–$C_4$ alkyl, acetyl, phenyl; or $R^1$ and $R^2$ may be taken together to form a ring such as triazole, 4-methylpiperazine, or morpholine;

$R^4$ and $R^7$ are independently selected from the group:
hydrogen;
$C_1$–$C_8$ alkyl substituted with 0–3 $R^{11}$; $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ and $R^{11A}$ are independently selected at each occurrence from the group: H, —$CH_2NR^{13}R^{14}$, —$NR^{13}R^{14}$, —$OR^{13}$, —$S(O)_mR^{13}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, boronic acid, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, 2-(1-morpholino)ethoxy, azido;

$C_3$–$C_{10}$ cycloalkyl substituted with 0–2 $R^{12}$;
$C_1$–$C_4$ alkyl substitued with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$; $C_5$–$C_{14}$ carbocyclic residue substituted with 0–3 $R^{12}$;
a 5- to 10-membered heterocyclic ring system containing 1 to 4 heteroatoms independently selected from oxygen, nitrogen or sulfur, said
heterocyclic ring system being substituted with 0–3 $R^{12}$;

$R^{12}$, when a substituent on carbon, is independently selected at each occurrence from the group:
phenyl, benzyl, phenethyl, phenoxy, benzyloxy, nitro, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14}$, 2-(1-morpholino)ethoxy; or a 5- or 6-membered heterocyclic ring containing from 1 to 4 heteroatoms independently selected from oxygen, nitrogen or sulfur;

or $R^{12}$ may be a 3- or 4-carbon chain attached to adjacent carbons on the ring to form a fused 5- or 6-membered ring, said 5- or 6-membered ring being, optionally substituted on the aliphatic carbons with $C_1$–$C_4$ alkyl, $C_1$–$C_4$ alkoxy; or —$NR^{13}R^{14}$; or when $R^{12}$ is attached to sulfur it may be =O;

$R^{12}$, when a substituent on nitrogen, is independently selected at each occurrence from the group:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group:
H;
phenyl substituted with 0–3 $R^{11A}$;
benzyl substituted with 0–3 $R^{11A}$;
$C_1$–$C_6$ alkyl substituted with 0–3 $R^{11A}$;
an amine protecting group when $R^{13}$ is bonded to N;
a hydroxy protecting group when $R^{13}$ is bonded to O;

$R^{14}$ is independently selected at each occurrence from the group: hydrogen, hydroxy, $C_1$–$C_6$ alkyl substituted with 0–3 groups selected from OH, $C_1$–$C_4$ alkoxy, $NH_2$, —$NH(C_1$–$C_4$ alkyl), $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$.

[2] Preferred compounds of [1] are those wherein:

$R^4$ and $R^7$ are independently selected at each occurrence from the group:
hydrogen;
$C_1$–$C_8$ alkyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ partially unsaturated carbocyclic residue substituted with 0–3 $R^{12}$;
a 5- to 6-membered heterocyclic ring system containing 1 to 3 heteroatoms independently selected from oxygen, nitrogen or sulfur, said heterocyclic ring system being substituted with 0–2 $R^{12}$.

[3] More preferred compounds of [1] are those wherein:

$R^4$ and $R^7$ are independently selected at each occurrence from the group:
hydrogen;
$C_1$–$C_4$ alkyl substituted with 0–3 $R^{11}$;

$R^{11}$ is independently selected at each occurrence from the group:
H, cyano, —$CH_2NR^{13}R^{14}$, —$NR^{13}R^{14}$, —$OR^{13}$, $C_2$–$C_4$ alkoxyalkyl, —$S(O)_mR^{13}$, $C_1$–$C_4$ alkyl, $C_3$–$C_{10}$ cycloalkyl;
a $C_5$–$C_{14}$ saturated or partially unsaturated carbocyclic residue substituted with 0–3 $R^{12}$;
aryl($C_1$–$C_3$ alkyl)-substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is independently selected at each occurrence from the group:
phenyl, benzyl, phenethyl, phenoxy, benzyloxy, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, 2-(1-morpholino) ethoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, —$S(O)_mR^{13}$, —$SO_2NR^{13}R^{14}$; or a 5- or 6-membered heterocyclic ring containing from 1 to 4 heteroatoms independently selected from oxygen, nitrogen or sulfur;
or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —$NR^{13}R^{14}$;
or when $R^{12}$ is attached to sulfur it may be =O;

$R^{12}$, when a substituent on nitrogen, is independently selected at each occurrence from the group: phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group: H, $C_1$–$C_6$ alkyl, $C_3$–$C_6$ alkoxyalkyl, phenyl, or benzyl;

$R^{14}$ is independently selected at each occurrence from the group: OH, H, $CF_3$, $C_1$–$C_4$ alkyl, $C_1$–$C_4$ alkoxy, $NH_2$, phenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—.

[4] Most preferred compounds of [1] are those wherein:

$R^4$ and $R^7$ are independently selected at each occurrence from the group: benzyl, fluorobenzyl, pyrrolylmethyl, methoxybenzyl, isobutyl, nitrobenzyl, aminobenzyl, thienylmethyl, hydroxybenzyl, pyridylmethyl, or naphthylmethyl;

$R^4$ and $R^7$ are both benzyl, isobutyl, 4-nitrobenzyl, 4-fluorobenzyl, 3-methoxybenzyl, 4-methoxybenzyl, 4-hydroxybenzyl, 4-(2-hydroxyethoxy)benzyl, 4-(2-morpholinylethoxy)benzyl, 3-($H_2NC$(=O)$CH_2O$) benzyl, 3,4-difluorobenzyl, 2-naphthylmethyl, 2-thienylmethyl, 4-methylthiobenzyl, isopropyl, or 4-pyridylmethyl;

$R^4$ is 4-nitrobenzyl and $R^7$ is 2-nitrobenzyl; and
$R^4$ is 4-aminobenzyl and $R^7$ is 2-aminobenzyl.

[5] Also provided by this invention is a process for the preparation of a compound of the formula (II):

(II)

wherein:
$R^1$ and $R^2$ are independently selected from the group: $C_1$–$C_4$ alkyl, acetyl, phenyl; or $R^1$ and $R^2$ may be taken together to form a ring such as triazole, 4-methylpiperazine, or morpholine;

$R^4$ and $R^7$ are independently selected from the group:
hydrogen;
$C_1$–$C_8$ alkyl substituted with 0–3 $R^{11}$;
$C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ and $R^{11A}$ are independently selected at each occurrence from the group:
H, —$CH_2NR^{13}R^{14}$, —$NR^{13}R^{14}$, —$OR^{13}$, —$S(O)_mR^{13}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, boronic acid, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, 2-(1-morpholino)ethoxy, azido;
$C_3$–$C_{10}$ cycloalkyl substituted with 0–2 $R^{12}$;
$C_1$–$C_4$ alkyl substitued with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
$C_5$–$C_{14}$ carbocyclic residue substituted with 0–3 $R^{12}$;
a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is independently selected at each occurrence from the group:
phenyl, benzyl, phenethyl, phenoxy, benzyloxy, nitro, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14}$, 2-(1-morpholino)ethoxy; or
a 5- or 6-membered heterocyclic ring containing from 1 to 4 heteroatoms independently selected from oxygen, nitrogen or sulfur;
or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy; or —$NR^{13}R^{14}$; or
when $R^{12}$ is attached to sulfur it may be =O;

$R^{12}$, when a substituent on nitrogen, is independently selected at each occurrence from the group:
phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group:
H;
phenyl substituted with 0–3 $R^{11A}$;
benzyl substituted with 0–3 $R^{11A}$;
$C_1$–$C_6$ alkyl substituted with 0–3 $R^{11A}$;
an amine protecting group when $R^{13}$ is bonded to N;
a hydroxy protecting group when $R^{13}$ is bonded to O;

$R^{14}$ is independently selected at each occurrence from the group: hydrogen, hydroxy, $C_1$–$C_6$ alkyl substituted with 0–3 groups selected from OH, $C_1$–$C_4$ alkoxy, $NH_2$, —$NH(C_1$–$C_4$ alkyl), $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

said method comprising the steps:

(a) contacting a compound of the formula (I)

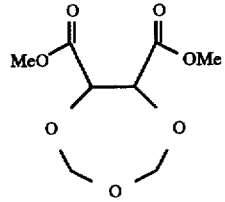

with an ester reducing agent in a nonpolar aprotic solvent, for a period of time ranging from 1 to 24 hours, at a temperature between –100° and –10° C., under an inert atmosphere to form the corresponding dialdehyde; and (b) contacting said dialdehyde with a hydrazine of the formula $H_2NNR^1R^2$, wherein $R^1$ and $R^2$ are as defined above, in a nonpolar aprotic solvent, at a temperature between –5° and 5° C., under an inert atmosphere.

[6] Also provided by this invention is a process for the preparation of a compound of the formula (III):

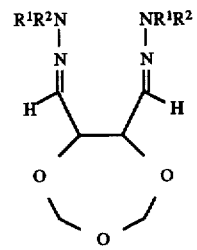

wherein:
$R^1$ and $R^2$ are independently selected from the group: $C_1$–$C_4$ alkyl, acetyl, phenyl; or $R^1$ and $R^2$ may be taken together to form a ring such as triazole, 4-methylpiperazine, or morpholine;

$R^4$ and $R^7$ are independently selected from the group: hydrogen;
$C_1$–$C_8$ alkyl substituted with 0–3 $R^{11}$;
$C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ and $R^{11A}$ are independently selected at each occurrence from the group:
H, —$CH_2NR^{13}R^{14}$, —$NR^{13}R^{14}$, —$OR^{13}$, —$S(O)_mR^{13}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, boronic acid, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, 2-(1-morpholino)ethoxy, azido;
$C_3$–$C_{10}$ cycloalkyl substituted with 0–2 $R^{12}$;
$C_1$–$C_4$ alkyl substitued with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
$C_5$–$C_{14}$ carbocyclic residue substituted with 0–3 $R^{12}$;

9 a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$ when a substituent on carbon, is independently selected at each occurrence from the group:

phenyl, benzyl, phenethyl, phenoxy, benzyloxy, nitro, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14b}$ · 2-(1-morpholino)ethoxy; or a 5- or 6-membered heterocyclic ring containing from 1 to 4 heteroatoms independently selected from oxygen, nitrogen or sulfur;

or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy; or —$NR^{13}R^{14}$; or when $R^{12}$ is attached to sulfur it may be =O;

$R^{12}$, when a substituent on nitrogen, is independently selected at each occurrence from the group:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group:

H;

phenyl substituted with 0–3 $R^{11A}$;

benzyl substituted with 0–3 $R^{11}A$;

$C_1$–$C_6$ alkyl substituted with 0–3 $R^{11A}$;

an amine protecting group when $R^{13}$ is bonded to N;

a hydroxy protecting group when $R^{13}$ is bonded to O;

$R^{14}$ is independently selected at each occurrence from the group: hydrogen, hydroxy, $C_1$–$C_6$ alkyl substituted with 0–3 groups selected from OH, $C_1$–$C_4$ alkoxy, $NH_2$, —$NH(C_1$–$C_4$ alkyl), $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

said method comprising the steps:

10

(a) contacting a compound of the formula (I)

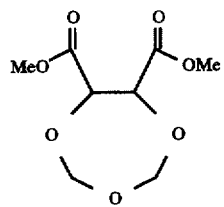

(I)

with an ester reducing agent in a nonpolar aprotic solvent, for a period of time ranging from 1 to 24 hours, at a temperature between −100° and −10° C., under an inert atmosphere to form the corresponding dialdehyde;

(b) contacting said dialdehyde with a hydrazine of the formula $H_2NNR^1R^2$, wherein $R^1$ and $R^2$ are as defined above, in a nonpolar aprotic solvent, at a temperature between −5° and 5° C., under an inert atmosphere; and (c) contacting said compound of the formula (II) with a nucleophile of the formula $R^4$—M and/or $R^7$—M, wherein M is a metal or metal-halide and wherein $R^4$ and $R^7$ are as defined above, in a nonpolar aprotic solvent, for a time period ranging from about 1 minute to 24 hours, at a
temperature between −78° and 25°, in an inert atmosphere.

[7] Also provided by this invention is a process for the preparation of a compound of the formula (IV):

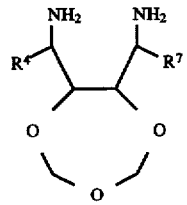

(IV)

wherein:

$R^1$ and $R^2$ are independently selected from the group: $C_1$–$C_4$ alkyl, acetyl, phenyl; or $R^1$ and $R^2$ may be taken together to form a ring such as triazole, 4-methylpiperazine, or morpholine;

$R^4$ and $R^7$ are independently selected from the group: hydrogen;

$C_1$–$C_8$ alkyl substituted with 0–3 $R^{11}$;

$C_3$–$C_{14}$ carbocyclic ring system substituted with 0–3 $R^{11}$ or 0–3 $R^{12}$;

a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ and $R^{11A}$ are independently selected at each occurrence from the group:

H, —$CH_2NR^{13}R^{14}$, —$NR^{13}R^{14}$, —$OR^{13}$, —$S(O)_mR^{13}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, boronic acid, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, 2-(1-morpholino)ethoxy, azido;

$C_3$-$C_{10}$ cycloalkyl substituted with 0-2 $R^{12}$;
$C_1$-$C_4$ alkyl substitued with 0-2 $R^{12}$;
aryl($C_1$-$C_3$ alkyl)-, substituted with 0-2 $R^{12}$;
$C_2$-$C_6$ alkoxyalkyl-, substituted with 0-2 $R^{12}$;
$C_5$-$C_{14}$ carbocyclic residue substituted with 0-3 $R^{12}$;
a 5- to 10-membered heterocyclic ring system containing 1 to 4 heteroatoms independently selected from oxygen, nitrogen or sulfur, said heterocyclic ring system being substituted with 0-3 $R^{12}$;

$R^{12}$, when a substituent on carbon, is independently selected at each occurrence from the group:
phenyl, benzyl, phenethyl, phenoxy, benzyloxy, nitro, $C_1$-$C_4$ alkyl, $C_3$-$C_6$ cycloalkyl, $C_3$-$C_6$ cycloalkylmethyl, $C_7$-$C_{10}$ arylalkyl, $C_1$-$C_4$ alkoxy, $C_3$-$C_6$ cycloalkoxy, —$OR^{13}$, $C_1$-$C_4$ alkyl substituted with —$NR^{13}R^{14}$, —$NR^{13}R^{14}$, $C_2$-$C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14}$, 2-(1-morpholino) ethoxy; or
a 5- or 6-membered heterocyclic ring containing from 1 to 4 heteroatoms independently selected from oxygen, nitrogen or sulfur;
or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$-$C_4$ alkyl, $C_1$-$C_4$ alkoxy; or
—$NR^{13}R^{14}$; or
when $R^{12}$ is attached to sulfur it may be =O;

$R^{12}$, when a substituent on nitrogen, is independently selected at each occurrence from the group:
phenyl, benzyl, phenethyl, $C_1$-$C_4$ alkoxy, $C_1$-$C_4$ alkyl, $C_3$-$C_6$ cycloalkyl, $C_3$-$C_6$ cycloalkylmethyl, —$CH_2NR^{13}R^{14}$, —$NR^{13}R^{14}$, $C_2$-$C_6$ alkoxyalkyl;

$R^{13}$ is independently selected at each occurrence from the group:
H;
phenyl substituted with 0-3 $R^{11A}$;
benzyl substituted with 0-3 $R^{11A}$;
$C_1$-$C_6$ alkyl substituted with 0-3 $R^{11A}$;
an amine protecting group when $R^{13}$ is bonded to N;
a hydroxy protecting group when $R^{13}$ is bonded to O;

$R^{14}$ is independently selected at each occurrence from the group: hydrogen, hydroxy, $C_1$-$C_6$ alkyl substituted with 0-3 groups selected from OH, $C_1$-$C_4$ alkoxy, $NH_2$, —$NH(C_1$-$C_4$ alkyl), $C_1$-$C_6$ alkoxy, $C_2$-$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —($CH_2$)$_4$—, —($CH_2$)$_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1$-$C_6$ alkyl;

$R^{13A}$ and $R^{14A}$ can alternatively join to form —($CH_2$)$_4$—, —($CH_2$)$_5$—, —$CH_2CH_2N(R^{15})CH_2CH_2$—, or —$CH_2CH_2OCH_2CH_2$—;

$R^{15}$ is H or $CH_3$;

said method comprising the steps:

(a) contacting a compound of the formula (I)

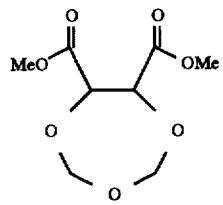

(I)

with an ester reducing agent in a nonpolar aprotic solvent, for a period of time ranging from 1 to 24 hours, at a temperature between −100° and −10° C., under an inert atmosphere to form the corresponding dialdehyde;

(b) contacting said dialdehyde with a hydrazine of the formula $H_2NNR^1R^2$, wherein $R^1$ and $R^2$ are as defined above, in a nonpolar aprotic solvent, at a temperature between −5° and 5° C., under an inert atmosphere; and (c) contacting said compound of the formula (II) with a nucleophile of the formula $R^4$—M and/or $R^7$—M, wherein M is a metal or metal-halide and wherein $R^4$ and $R^7$ are as defined above, in a nonpolar aprotic solvent, for a time period ranging from about 1 minute to 24 hours, at a temperature between −78° and 25°, in an inert atmosphere to form a compound of the formula (III):

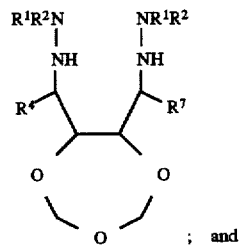

; and (d) contacting said compound of the formula (III) with a hydrazine reducing agent in a polar protic solvent, at a temperature between 0° and 200° C., at a pressure between 15–1000 psi.

[8] Also provided by this invention is a process for the preparation of a compound of the formula (V):

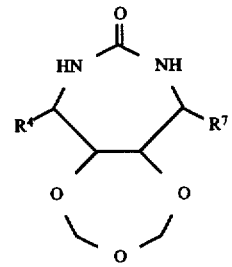

(V)

wherein:
$R^1$ and $R^2$ are independently selected from the group: $C_1$-$C_4$ alkyl, acetyl, phenyl; or $R^1$ and $R^2$ may be taken together to form a ring such as triazole, 4-methylpiperazine, or morpholine;

$R^4$ and $R^7$ are independently selected from the group: hydrogen;
$C_1$-$C_8$ alkyl substituted with 0-3 $R^{11}$;

$C_3-C_{14}$ carbocyclic ring system substituted with 0–3 $R^{11}$ or 0–3 $R^{12}$;

a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ and $R^{11A}$ are independently selected at each occurrence from the group:

H, —$CH_2NR^{13}R^{14}$, —$NR^{13}R^{14}$, —$OR^{13}$, —$S(O)_mR^{13}$, —$NR^{14}SO_2NR^{13}R^{14}$, —$NR^{14}SO_2R^{13}$, —$SO_2NR^{13}R^{14}$, $C_1-C_4$ alkyl, $C_2-C_4$ alkenyl, $C_3-C_6$ cycloalkylmethyl, benzyl, phenethyl, phenoxy, benzyloxy, nitro, $C_7-C_{10}$ arylalkyl, boronic acid, $C_3-C_6$ cycloalkoxy, $C_1-C_4$ alkyl substituted with —$NR^{13}R^{14}$, $C_1-C_4$ hydroxyalkyl, methylenedioxy, ethylenedioxy, 2-(1-morpholino)ethoxy, azido;

$C_3-C_{10}$ cycloalkyl substituted with 0–2 $R^{12}$;

$C_1-C_4$ alkyl substitued with 0–2 $R^{12}$;

aryl($C_1-C_3$ alkyl)-, substituted with 0–2 $R^{12}$;

$C_2-C_6$ alkoxyalkyl-, substituted with 0–2 $R^{12}$;

$C_5-C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is independently selected at each occurrence from the group:

phenyl, benzyl, phenethyl, phenoxy, benzyloxy, nitro, $C_1-C_4$ alkyl, $C_3-C_6$ cycloalkyl, $C_3-C_6$ cycloalkylmethyl, $C_7-C_{10}$ arylalkyl, $C_1-C_4$ alkoxy, $C_3-C_6$ cycloalkoxy, —$OR^{13}$, $C_1-C_4$ alkyl substituted with —$NR^{13}R^{14}$, —$NR^{13}R^{14}$, $C_2-C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14}$, 2-(1-morpholino) ethoxy; or a 5- or 6-membered heterocyclic ring containing from 1 to 4 heteroatoms independently selected from oxygen, nitrogen or sulfur;

or $R^{12}$ may be a 3- or 4-carbon chain attached to adjacent carbons on the ring to form a fused 5- or 6-membered ring, said 5- or 6-membered ring being optionally substituted on the aliphatic carbons with $C_1-C_4$ alkyl, $C_1-C_4$ alkoxy; or
—$NR^{13}R^{14}$; or when $R^{12}$ is attached to sulfur it may be =O;

$R^{12}$, when a substituent on nitrogen, is independently selected at each occurrence from the group:

phenyl, benzyl, phenethyl, $C_1-C_4$ alkoxy, $C_1-C_4$ alkyl, $C_3-C_6$ cycloalkyl, $C_3-C_6$ cycloalkylmethyl, —$CH_2NR^{13}R^{14}$, —$NR^{13}R^{14}$, $C_2-C_6$ alkoxyalkyl;

$R^{13}$ is independently selected at each occurrence from the group:

H;

phenyl substituted with 0–3 $R^{11A}$;

benzyl substituted with 0–3 $R^{11A}$;

$C_1-C_6$ alkyl substituted with 0–3 $R^{11A}$;

an amine protecting group when $R^{13}$ is bonded to N;

a hydroxy protecting group when $R^{13}$ is bonded to O;

$R^{14}$ is independently selected at each occurrence from the group: hydrogen, hydroxy, $C_1-C_6$ alkyl substituted with 0–3 groups selected from OH, $C_1-C_4$ alkoxy, $NH_2$, —$NH(C_1-C_4$ alkyl), $C_1-C_6$ alkoxy, $C_2-C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1-C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

said method comprising the steps:

(a) contacting a compound of the formula (I)

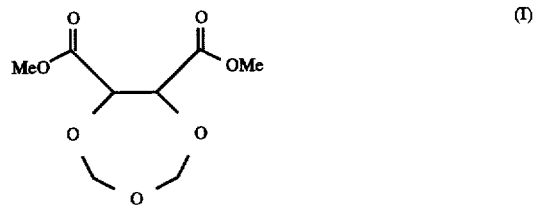

with an ester reducing agent in a nonpolar aprotic solvent, for a period of time ranging from 1 to 24 hours, at a temperature between −100° and −10° C., under an inert atmosphere to form the corresponding dialdehyde;

(b) contacting said dialdehyde with a hydrazine of the formula $H_2NNR^1R^2$, wherein $R^1$ and $R^2$ are as defined above, in a nonpolar aprotic solvent, at a temperature between −5° and 5° C., under an inert atmosphere; and (c) contacting said compound of the formula (II) with a nucleophile of the formula $R^4$—M and/or $R^7$—M, wherein M is a metal or metal-halide and wherein $R^4$ and $R^7$ are as defined above, in a nonpolar aprotic solvent, for a time period ranging from about 1 minute to 24 hours, at a temperature between −78° and 25°, in an inert atmosphere to form a compound of the formula (III):

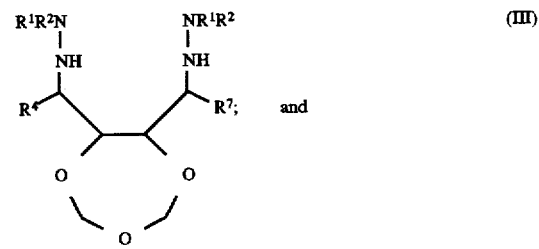

(d) contacting said compound of the formula (III) with a hydrazine reducing agent in a polar protic solvent, at a temperature between 0° and 200° C., at a pressure between 15–1000 psi to form a compound of the formula (IV):

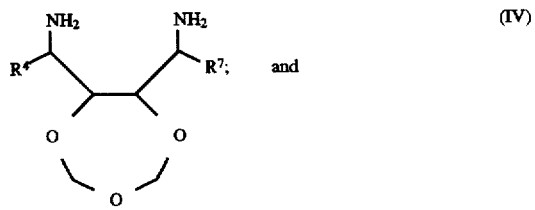

(e) contacting said compound of formula (IV) with at least one equivalent of a suitable cyclizing agent, optionally in the presence of a hindered amine base, in an aprotic solvent.

[9] Preferred is the the process of [5] wherein:
for step (a):
the reaction temperature is –50° to –40° C.;
the reaction time is 0.5 to 5 hrs;
the reaction solvent is selected from the group: benzene, toluene, tetrahydrofuran, diethoxymethane, and methyl tert-butyl ether; and
the ester reducing agent is selected from the group: bis(N-methylpiperazinyl)aluminum hydride; diisobutylaluminum hydride; sodium aluminum hydride; sodium bis(2-methoxyethoxy)aluminum hydride and tributlytin hydride; and
for step (b):
the reaction solution is preferably warmed to –5° to 5° C.;

[10] Preferred is the the process of [6] wherein
for step (a):
the reaction temperature is –50° to –40° C.;
the reaction time is 0.5 to 5 hrs;
the reaction solvent is selected from the group: benzene, toluene, tetrahydrofuran, diethoxymethane, and methyl tert-butyl ether;
the ester reducing agent is selected from the group: bis(N-methylpiperazinyl)aluminum hydride; diisobutylaluminum hydride; sodium aluminum hydride; sodium bis(2-methoxyethoxy)aluminum hydride or tributlytin hydride;
for step (b):
the reaction solution is warmed to –5° to 5° C.; and
for step (c):
the reaction temperature is –25° to –15° C.;
the reaction solvent is selected from the group: benzene, tetrahydrofuran, hexanes, cyclohexanes or toluene;
4–7 molar equivalents of either $R^4$—M or $R^7$—M are used wherein M is selected from lithium(I) and potassium(I).

[11] Preferred is the the process of [7] wherein:
for step (a):
the reaction temperature is –50° to –40° C.;
the reaction time is 0.5 to 5 hrs;
the reaction solvent is selected from the group: benzene, toluene, tetrahydrofuran, diethoxymethane, and methyl tert-butyl ether;
the ester reducing agent is selected from the group: bis(N-methylpiperazinyl)aluminum hydride; diisobutylaluminum hydride; sodium aluminum hydride; sodium bis(2-methoxyethoxy)aluminum hydride or tributlytin hydride;
for step (b):
the reaction solution is warmed to –5° to 5° C.; and
for step (c):
the reaction temperature is –25° to –15° C.;
the reaction solvent is selected from the group: benzene, tetrahydrofuran, hexanes, cyclohexanes or toluene;
4–7 molar equivalents of either $R^4$—M or $R^7$—M are used wherein M is selected from lithium(I) and potassium(I); and
for step (d):
the hydrazine reduction is carried out using catalytic hydrogenolysis or dissolving metal reduction; and
the solvent utilized for catalytic hydrogenation is selected from the group:
water, toluene, methanol, ethanol, 2-propanol, n-butanol, isobutanol, and other lower alcohols.

[12] Preferred is the process of [8] wherein:
for step (a):
the reaction temperature is –50° to –40° C.;
the reaction time is 0.5–5 hrs; the reaction solvent is selected from the group: benzene, toluene, tetrahydrofuran, diethoxymethane, and methyl tert-butyl ether;
the ester reducing agent is selected from the group: bis(N-methylpiperazinyl)aluminum hydride; diisobutylaluminum hydride; sodium aluminum hydride; sodium bis(2-methoxyethoxy)aluminum hydride or tributlytin hydride;
for step (b):
the reaction solution is warmed to –5° to 5° C.; and
for step (c):
the reaction temperature is –25° to –15° C.;
the reaction solvent is selected from the group: benzene, tetrahydrofuran, hexanes, cyclohexanes or toluene;
4–7 molar equivalents of either $R^4$—M or $R^7$—M are used wherein M is selected from lithium(I) and potassium(I); and
for step (d):
the hydrazine reduction is carried out using catalytic hydrogenolysis or dissolving metal reduction; and
the solvent utilized for catalytic hydrogenation is selected from the group:
water, toluene, methanol, ethanol, 2-propanol, n-butanol, isobutanol, and other lower alcohols; and
for step (e):
the reaction temperature is –5° to 0° C.;
the cyclizing reagent is selected from the group: phosgene, carbonyl diimidazole, disuccinimidyl carbonate, C1–C4 dialkyl carbonate, ethylene carbonate, or vinylene carbonate;
the cyclizing agent is added at a temperature below 0° C., followed by warming of the reaction mixture to 20°–25° C.;
the reaction solvent is selected from the group: toluene, acetonitrile, tetrahydrofuran, methyl tert-butyl ether, diethoxymethane, ethyl acetate, 1,1,2,2-tetrachloroethane, or methylene chloride;
the optionally present hindered amine base is selected from the group: aromatic amines; heteroaromatic amines; pyridine; trialkyl amines; triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2 ]octane (DABCO); 1,8-diazabicyclo[5.4.0 ]undec-7-ene (DBU); tetramethylethylenediamine (TMEDA); or substituted pyridines such as N,N-dimethylaminopyridine (DMAP), 4-pyrrolidinopyridine, 4-piperidinopyridine.

[13] More preferred is the process of [5] wherein:
for step (a):
the reaction solvent is toluene;
the ester reducing agent is diisobutlyaluminum hydride.

[14] More preferred is the process of [6] wherein:
for step (a):
the reaction solvent is toluene;
the ester reducing agent is diisobutlyaluminum hydride; and for step (c):
  the reaction solvent is toluene;
[15] More preferred is the process of [7] wherein:
  for step (a):
    the reaction solvent is toluene;
    the ester reducing agent is diisobutlyaluminum hydride;
  for step (c):
    the reaction solvent is toluene; and
  for step (d):
    the reducing agent is Raney nickel with hydrogen;
    the reaction solvent is selected from the group methanol and ethanol;
    the reaction pressure is 180–250 psi;
    the reaction temperature is 80°–120° C.;
    the reaction time is 1–48 hrs.
[16] More preferred is the process of [8] wherein:
  for step (a):
    the reaction solvent is toluene;
    the ester reducing agent is diisobutlyaluminum hydride;
  for step (c):
    the reaction solvent is toluene;
  for step (d):
    the hydrazine reducing agent is Raney nickel with hydrogen;
    the reaction solvent is methanol or ethanol;
    the reaction pressure is 180–250 psi;
    the reaction temperature is 80°–120° C.;
    the reaction time is 1–48 hrs.; and
  for step (5):
    the cyclizing reagent is carbonyldiimidazole;
    the reaction solvent is acetonitrile; and
    the optionally present hindered amine base is triethylamine.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$ through $R^{14}$, $R^4$ and $R^7$, m, n, etc.) occurs more than one time in any constituent or in formula (II), (III), (IV), or (V), or any other formula herein, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, for example, in —N($R^{20}$)$_2$, each of the $R^{20}$ substituents may be independently selected from the list of possible $R^{20}$ groups defined. Also, combinations of substituents and/or variables are permissible only if such combinations result in stable compounds. Similarly, by way of example, for the group —C($R^{11}$)$_2$—, each of the two $R^{11}$ substituents on C is independently selected from the defined list of possible $R^{11}$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of formula (IX). Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic.

Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, or isatinoyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

When a bond to a substituent is shown to cross the bond connecting two atoms in a ring, then such substituent may be bonded to any atom on the ring. When a substituent is listed without indicating the atom via which such substituent is bonded to the rest of the compound of formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of formula (II), (III), (IV), or (V) via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, phosphate esters, $C_1$-$C_6$ alkyl substituted with 0–3 $R^{11}$, $C_3$-$C_6$ alkoxyalkyl substituted with 0–3 $R^{11}$, $C_1$-$C_6$ alkylcarbonyl substituted with 0–3 $R^{11}$, $C_1$-$C_6$ alkoxycarbonyl substituted with 0–3 $R^{11}$, $C_1$-$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or heteroarylcarbonyl. Examples of groups that, when administered to a mammalian subject, are cleaved to form a free hydroxyl, amino or sulfhydryl, may include hydroxy, amine or sulfhydryl protecting groups, respectively.

As used herein, the term "ester reducing agent" means any reagent or combination of reagents capable of reducing esters to aldehydes directly or esters to aldehydes indirectly via a combination of reduction to the alcohol followed by oxidation to the aldehyde. Exemplary ester reducting agents that convert esters to aldehydes directly include: bis(N-methylpiperazinyl)aluminum hydride; diisobutylaluminum hydride; sodium aluminum hydride; sodium bis(2-methoxyethoxy)aluminum hydride and tributlytin hydride. Exemplary ester reducing agents that convert esters to aldehydes indirectly (via reduction to the alcohol followed by oxidation to the aldehyde) include: for reduction to the alcohol (9-borabicyclo[3.3.1]nonane, borane-dimethylsulfide, diisobutylaluminum hydride, lithium aluminum hydride, lithium-ammonia, lithium 9-borabicyclo [3.3.1]nonane, lithium borohydride, lithium triethylborohydride, sodium borohydride, and 2,3-dimethyl-2-butylborane); and for oxidation of the alcohol to the aldehyde (chromium (IV) oxide-pyridine, potassium dichromate, pyridiniumchlorochromate, pyridiniumdichromate, barium manganate, chlorodimethylsulfonium chloride, and dimethylsulfoxidedicyclohexylcarbodiimide).

As used herein, the term "nucleophile" means any organometallic species that can add to hydrazones of the structure of compound (II). Exemplary nucleophiles include, by way of example and without limitation: benzyllithium, n-butyllithium, sec-butyllithium, tert-butyllithium, methylmagnesium bromide, vinyllithium, allyllithium, ethyllithium, phenylthiomethyllithium, 2-furyllithium, butynyllithium, benzylmagnesium chloride, and phenylmagnesum chloride; said nucleophiles being optionally substituted.

As used herein, the term "hydrazine reducing agent" means any such reagent and/or conditions or combinations of such reagents and/or conditions that may be used to convert a hydrazine group to an amine. Exemplary hydrazine reducing agents include, by way of example and without limitation: Raney nickel and hydrogen; zinc and hydrochloric acid; sodium hydrosulfite; and dissolving metal such as lithium in ammonia.

As used herein, the term "strong bases" means any organometallic species capable of deprotonating $R^4$—H and $R^7$—H. Exemplary strong bases include, by way of example and without limitation: n-butyllithium, sec-butyllithium, tert-butyllithium, lithium diisopropylamide, lithium tetramethylpiperazine, lithium hydride, lithium hexamethyldisilylamide, and potassium alkoxide with alkyllithium, e.g. potassium tert-butoxide with n-butyllithium.

As used herein, the term "activator" is intended to mean any agent capable of accelerating the deprotonation of $R^4$—H and/or $R^7$—H with a strong base. Exemplary activators include, by way of example and without limitation: tetrahydrofuran; aromatic amines, such as pyridine; trialkyl amines such as triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, 4-piperidinopyridine.

As used herein, the term "cyclizing reagent" means any reagent or combination of reagents that will effect the formation of a cyclic urea from a linear diamine. Exemplary cyclizing reagents include, by way of example and without limitation: phosgene, carbonyl diimidazole, disuccinimidyl carbonate, $C_1$–$C_4$ dialkyl carbonate, ethylene carbonate, and vinylene carbonate.

As used herein, the term "amine protecting group" means any group known in the art of organic synthesis for the protection of amine groups which is stable to an ester reducing agent, a disubstituted hydrazine, $R^4$—M and $R^7$—M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (Fmoc); (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As used herein, a "hindered amine base" is intended to include any of a number of nitrogen containing bases wherein the nitrogen is surrounded by sterically demanding groups so that the nitrogen accessibility is reduced. Examples of hindered amine bases useful for the present invention include aromatic amines, such as pyridine; trialkyl amines such as triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, 4-piperidinopyridine.

By a "ketal ring" or "ketal" group is meant any ketal protecting group which can be hydroyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene and Wuts, "Protective Groups in Organic Synthesis" John Wiley & Sons, New York (1991).

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The processes provided by the present invention may be further understood by referring to Scheme 1.

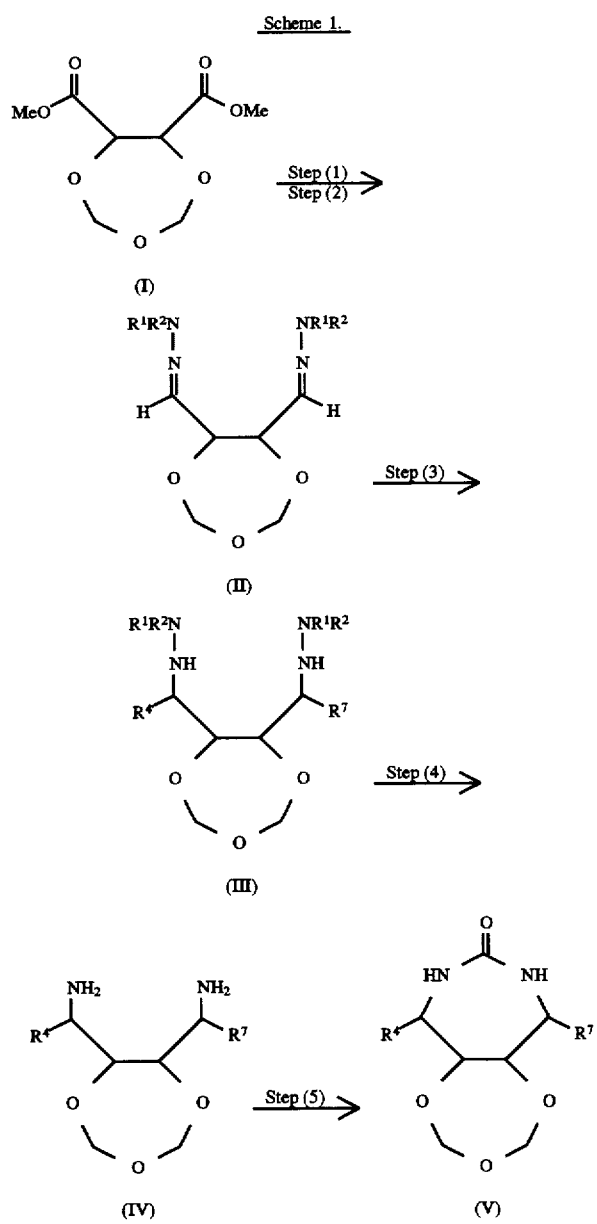

Steps (1) and (2): Aldehyde and Hydrazone Formation: Preparation of Compound (II):

These steps comprise the reduction of compound (I) to a dialdehyde using an ester reducing agent followed by the insitu formation of compound (II) by treatment of the dialdehyde with a hydrazine. In step (1), compound (I) is contacted in a nonpolar aprotic solvent, with agitation at −100° to −10° C. for 1–24 hr under an inert atmosphere, with 2–3 molar equivalents of an ester reducing agent to form a dialdehyde intermediate which is carried through, without isolation and following a reaction quench with 2–3 molar equivalents of a proton donor, to step (2). In step (2), the dialdehyde intermediate is warmed to −5° to 5° C. and contacted with agitation in an inert atmosphere with at least 2–3 molar equivalents of a hydrazine of the formula $R^1R^2NNH_2$ to form compound (II) which is optionally isolated.

The preferred reaction temperature for step (1) is −50° to −40° C.

The preferred reaction time for step (1) is 0.5–5 hrs.

The preferred solvents for step (1) include benzene, toluene, tetrahydrofuran, diethoxymethane, and methyl tert-butyl ether. The more preferred solvent is toluene.

In step (1),the preferred ester reducing agents that convert esters to aldehydes directly include: bis(N-methylpiperazinyl)aluminum hydride; diisobutylaluminum hydride; sodium aluminum hydride; sodium bis(2-methoxyethoxy)aluminum hydride and tributyltin hydride. The preferred ester reducing agents that convert esters to aldehydes indirectly (via reduction to the alcohol followed by oxidation to the aldehyde) include: for reduction to the alcohol (9-borabicyclo[3.3.1]nonane, borane-dimethylsulfide, diisobutylaluminum hydride, lithium aluminum hydride, lithium-ammonia, lithium 9-borabicyclo [3.3.1]nonane, lithium borohydride, lithium triethylborohydride, sodium borohydride, and 2,3-dimethyl-2-butylborane); and for oxidation of the alcohol to the aldehyde (chromium (IV) oxide-pyridine, potassium dichromate, pyridiniumchlorochromate, pyridiniumdichromate, barium manganate, chlorodimethyl-sulfonium chloride, and dimethylsulfoxide-dicyclohexylcarbodiimide). The most preferred ester reducing agent is DIBAL-H. It is preferred that 2.2 molar equivalents of DIBAL-H be used.

The preferred proton donor for step (1) is an alcohol. The more preferred alcohol is methanol. It is preferred that 2.2 molar equivalents of methanol be used for the quench.

In step (2), it is preferred that the aldehyde solution be warmed to 0° C. prior to the hydrazone formation.

It is preferred that the reaction be conducted under an inert atmosphere throughout steps (1) and (2) until isolation of the hydrazone.

$R^1$ and $R^2$ are preferably $C_1$–$C_4$ alkyl, acetyl, phenyl, or taken together can form a ring such as triazole, 4-methylpiperazine, or morpholine.

It is preferred that compound (II) be isolated from the reaction mixture by filtering through a filter aid such as Celite and concentrating in vacuo.

Step (3): Hydrazine Formation: Preparation of Compound (III):

This step comprises alkylation of the hydrazone carbon with a nucleophile of the formula $R^4$—M and/or $R^7$—M. Compound (II) (1 molar equivalent) in an aprotic solvent at −78° to 25° C. in an inert atmosphere (in the presence of 0.5–10 molar equivalents of an activator) is contacted with 1–10 equivalents of a nucleophile $R^4$—M or $R^7$—M for 1 min to 24 hrs. to form compound (III) which is isolated. Compound (III) may optionally be purified by salt formation with an organic acid.

The preferred reaction temperature is −25° to −15° C.

The preferred reaction solvents include benzene, tetrahydrofuran, hexanes, cyclohexanes and toluene. The more preferred solvent in toluene.

R⁴—M or R⁷—M can be made by the action of 1 equivalent of a strong base on 1–20 equivalents of an optionally substituted R⁴—H or R⁷—H. Additionally, there are numerous other methods to prepare compounds of formulae R⁴—M or R⁷—M. These methods are well known to those skilled in the art. See, *Comprehensive Organic Synthesis*, B. M. Trost and I. Fleming, Pergamon, 1991, which is incorporated herein by reference.

R⁴ and R⁷ are preferably optionally substituted benzyllithium, n-butyllithium, sec-butyllithium, tert-butyllithium, methylmagnesium bromide, vinyllithium, allyllithium, ethyllithium, phenylthiomethyllithium, 2-furyllithium, butynyllithium, benzylmagnesium chloride, and phenylmagnesium chloride. It is preferred that 4–7 molar equivalents of R⁴ and/or R⁷ be used.

The preferred activators include: tetrahydrofuran; aromatic amines, such as pyridine; trialkyl amines such as triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, 4-piperidinopyridine. The more preferred activator is tetrahydrofuran. It is preferred that 3–5 molar equivalents of an activator be used.

It is preferred that the strong base be: an alkyllithium such as n-butyllithium, sec-butyllithium, tert-butyllithium; lithium diisopropylamide; lithium tetramethylpiperazine; lithium hydride; lithium hexamethyldisilylamide; or potassium alkoxide with alkyllithium, e.g. potassium tert-butoxide with n-butyllithium. The more preferred strong base is an alkyllithium.

M is preferably lithium(I) or potassium(I).

It is preferred that compound (III) be isolated from the reaction mixture by washing the reaction mixture with water and then following that with an acid base transfer with an aqueous inorganic or organic acid. The preferred acids include sulfuric acid, hydrochloric acid, trifluoroacetic acid, acetic acid, and phosphoric acid. These aqueous solutions may optionally be basified with alkali metal hydroxides, alkoxides, phosphates, or carbonates. The ensuing basified aqueous solutions may optionally be treated with water immiscible organic solvents to effect extraction of the compound (III) into organic solvents. Solvents preferred for the extraction of compound (III) from basified aqueous solutions include toluene, ethyl acetate, diethoxymethane, and methyl tert-butyl ether.

If purified by salt formation, it is preferred that the organic acid be sulfuric, methanesulfonic, dibenzoyltartaric, or oxalic acid.

Step (4): Amine Formation: Preparation of Compound (IV):

This step comprises the reduction of a hydrazine, with a hydrazine reducing agent, to an amine. Compound (III) in a polar protic solvent is contacted with agitation at 0°–200° C. under 15–1000 psi of pressure for a period of time with a hydrazine reducing agent, said agent being a hydrogen source and a reagent or combination of reagents suitable for effecting the reduction of a hydrazine bond while not effecting removal of the trioxepane, to form compound (IV) which is optionally isolated in the free base or salt form following removal of the reaction catalyst. The solvent(s) of choice will vary according to the reation conditions chosen to effect the amine formation. The reduction of the hydrazine to the amine may be effected using reductive conditions such as zinc in hydrochloric acid, catalytic hydrogenolysis with catalysts such as Raney nickel, hydroiodic acid, or by dissolving metal reductions.

The preferred hydrazine reducing agents are catalytic hydrogenolysis or dissolving metal reduction. If catalytic hydrogenolysis is chosen, the preferred hydrogen source is hydrogen gas and metal catalysts such as Raney nickel, platinum oxide, palladium on carbon, using heat and either high pressure 15 to 1000 psi or ultrasound or both. If a dissolving metal reduction is chosen the preferred reagents are lithium in ammonia. The more preferred hydrazine reducing agent is Raney nickel with hydrogen.

Preferred solvents for catalytic hydrogenation include water, toluene, methanol, ethanol, 2-propanol, n-butanol, isobutanol, and other lower alcohols. The more preferred solvents for catalytic hydrogenation are methanol and ethanol.

The preferred reaction pressure 180–250 psi.
The preferred reaction temperature is 80°–120° C.
The preferred reaction time is 1–48 hours.

If isolated as its salt, compound (IV) may be treated with organic acids. Preferred organic acids include benzenesulfonic acid, methanesulfonic acid, oxalic acid, and dibenzoyl tartaric acid. The more preferred acid is benzenesulfonic acid.

Step (5): Cyclic Urea Formation: Preparation of Compound (V):

This step comprises the cyclization of the linear diamine free base or salt to a cyclic urea. Compound (IV) in an aprotic solvent at −20°–30° C. in an inert atmosphere, optionally in the presence of 0–2 molar equivalents of a hindered amine base, is contacted with 1–1.5 molar equivalents of a suitable cyclizing reagent, which may optionally be added at a temperature lower than the reaction temperature, for 10 min to 3 days to form compound (V) which is isolated. Compound (V) may be optionally crystallized from organic solvent.

The preferred reaction temperature is 0° C.

The preferred cyclizing reagents include phosgene, carbonyl diimidazole, disuccinimidyl carbonate, C₁–C₄ dialkyl carbonate, ethylene carbonate, and vinylene carbonate. The more preferred cyclizing reagent is carbonyl diimidazole. It is preferred that 1.1 equivalents of cyclizing reagent be added.

It is preferred that the cyclizing agent be added at a temperature below 0° C. followed by warming of the reaction to 20°–25° C.

The preferred reaction solvents include toluene, acetonitrile, tetrahydrofuran, methyl tert-butyl ether, diethoxymethane, ethyl acetate, 1,1,2,2-tetrachloroethane, and methylene chloride. The more preferred solvent is acetonitrile.

If the salt form of the diamine is used in the reaction, it is preferred that a hindered base be added to the reaction. Preferred hindered amine bases include aromatic amines, such as pyridine; trialkyl amines such as triethylamine, N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, 4-piperidinopyridine. The more preferred hindered amine base is triethylamine. It is preferred that 1.1 molar equivalents of the hindered amine base be added.

It is preferred that compound (V) be isolated by solvent exchange to a water immiscible solvent, washing of the reaction mixture with a dilute acid, and washing of the reaction mixture with brine. The preferred water immiscible solvent is 4-methyl-2-pentanone. The preferred dilute acid is 1N hydrochloric acid.

The present invention may be specifically understood by reference to Scheme 2.

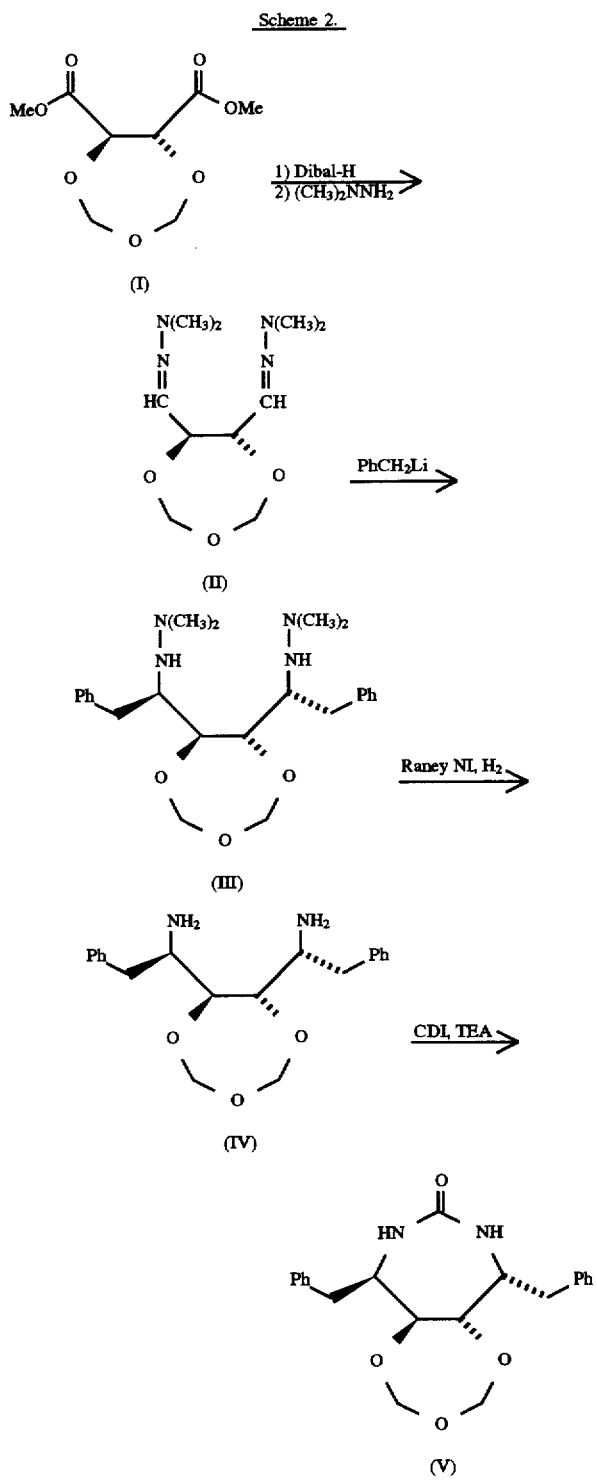

Scheme 2.

The disclosures of all of the references cited herein are hereby incorporated herein by reference in their entirety.

Using the procedures described above and outlined in Scheme 1 and Scheme 2 above, the following compounds were prepared. The following examples are meant to be illustrative of the present invention. These examples are not to be construed as limiting the invention's scope. With a judicious selection of reagents, as is well appreciated to one skilled in the art, these manipulations can be performed in a straightforward manner to yield the claimed combinations for compounds of the formulas (II), (III), (IV) and (V).

EXAMPLE 1 tetramethylhydrazone-1,3,5-trioxepane-6,7-dicarboxyaldehyde

Step (1):

Dimethyl-1,3,5-trioxepane-6,7-dicarboxylate (120 g, 0.545 mol) dissolved in toluene (1.05 L) under nitrogen and cooled to −50° C. in a flask fitted with mechanical stirring, an addition funnel and a temperature probe. Dibal-H (1.5M, 800 mL, 1.20 mmol) was dripped into the reaction mixture over 45 minutes. The reaction was stirred at −50° C. for an additional 90 min then methanol (53.4 mL, 1.3 mol) was added slowly.

Step (2):

The resulting gel was warmed to 0° C. whereupon it dissolved. Dimethyl hydrazine (91.1 mL, 1.20 mol) was added over 40 minutes and the reaction was warmed to room temperature. After stirring 45 minutes at room temperature a suspension of Celite (290 g) in water (145 mL) and heptane (1.8 L) was added andstirred for one hour. The reaction was filtered and rinsed with heptane (2×1.5 L). The filtrate was concentrated in vacuo and pumped to a brown oil (125.5 g, 94% yield).

EXAMPLE 2

(1,1'-[1,3,5-trioxepane-6,7-diylbis(phenylethylidene)]bis[2,2-dimethylhydrazine] free base isolated by acid/base transfer Step (3):

A 12 L flask was set up for dry reaction under nitrogen and charged with 1.72 L toluene. The system was degased by pulling a vacuum and then releaseing to nitrogen three times. The temperature was lowered to −20° C. secButyl lithium (1.3M in cyclohexane, 2.14 L, 2.78 mol) was charged followed by THF (0.68 L, 8.33 mol) maintaining the batch temperature at −21° to −14° C. A yellow solid crystallized out before the end of THF addition which took 40 minutes. After holding at −20° to −15° C. for an hour, a solution of tetramethylhydrazone-1,3,5-trioxepane-6,7-dicarboxaldehyde (96.9% wt, 250 g, 0.99 mol) in 450 mL toluene was charged over 25 minutes at −20° to −15° C. Sample drawn at 3 minutes after addition showed complete reaction. The mixture was stirred at <−17° C. for 35 minutes and then quenched into 5 L 1:1 water/ice. The layers were separated. The organic layer was washed with 3 L of water. Both aqueous layers showed a pH of >14; they were back extracted by 1.5 L of toluene. The toluene solutions were combined and extracted twice with 10% sulfuric acid (1.5 L and 0.5 L). Both aqueous extracts had a pH of <1. The combined acidic solution was back extracted with 2 L of toluene. The layers were separated, the aqueous layer was mixed with 2 L toluene and then basified with 50% KOH to a pH of >10 at 8°–15° C. There was some salt deposited out in the aqueous layer. The organic layer was washed twice with 2 L portions of water, and once with brine (1 L). The organic layer was concentrated and pumped overnight to 416.2 g of yellow oil, assayed 92.62% wt; yield=90.7%.

EXAMPLE 3

(1,1'-[1,3,5-trioxepane-6,7-diylbis(phenylethylidene)
]bis[2,2-dimethylhydrazine]sulfate (Part A) and
methanesulfonic acid (Part B) salts Step (3):

The benzyl lithium slurry was prepared from 0.29 mol of sec-butyl lithium as described in Example 1. To this slurry was charged a solution of tetramethylhydrazone-1,3,5-trioxepane-6,7-dicarboxaldehyde (90.6% wt, 25 g, 92.4 mmol) in 50 mL toluene at −20° to −15° C. After holding for half hour, the reaction was quenched into 500 mL 1:1 water/ice. The layers were separated and the organic layer was washed once with 300 mL water and once with 300 mL brine. The organic solution was concentrated on the rotovap. to 52.7 g yellow oil. Proton nmr showed 1,1'-[1,3,5-trioxepane-6,7-diylbis(phenylethylidene)]bis[2,2-dimethylhydrazine], a small amount of impurity, and about 17.7% wt (by integration) of toluene.

Part A. A portion of the above yellow oil (27.5 g<48 mmol of 1,1'-[1,3,5-trioxepane-6,7-diylbis(phenylethylidene)]bis[2,2-dimethylhydrazine]) was diluted with 17 mL toluene and 45 mL n-propanol and stirred at room temperature. To this solution was added 2.86 mL sulfuric acid (97%, 52 mmol) in 3 minutes. Temperature of the mixture went up to 46° C. and white solid deposited out within minutes. The mixture was stirred at ambient temperature for 10 minutes and in ice bath for 30 minutes. The solid was collected by filtration and rinsed with 1:1 toluene/n-propanol. The solid cake was dried by pulling air through it overnight to yield 21.5 g white solid, mp 190° C.(dec.).

Part B. Another portion of the above yellow oil (5 g <8.8 mmol of 1,1'-[1,3,5-trioxepane-6,7-diylbis(phenylethylidene)]bis[2,2-dimethylhYdrazine]) was diluted with 2.8 mL toluene and 11.4 mL acetonitrile and stirred at room temperature. To this solution was added 1.18 mL methanesulfonic acid (MSA, 99%, 18 mmol) in one minute. Temperature of the mixture rose to 46° C. and a clear solution was resulted. The mixture was stirred at ambient temperature and cooled slowly. At about 28° C. solid began to deposit out. The mixture was chilled in an ice bath for half hour. The solid was collected and rinsed by 1:1 toluene/acetonitrile and then dried by pulling air through the cake overnight to yield 4.7 g white solid.

EXAMPLE 2 aminopiperazine hydrazone of compound (II)

Trioxepane dimethyltartrate (10 g, 45 mmol) was dissolved in toluene (120 mL) and cooled to −50° C. DIBAL-H (1.5M toluene, 66 mL, 99 mmol) was added over 15 min and the reaction was stirred an additional 60 min at 40–45° C. Methanol (4.4 mL, 108 mmol) was added and the solution was warmed to 0° C. amd held for 15 min. Aminomethylpiperazine (11.9 mL, 99 mmol) was added over 10 minutes followed by ethyl acetate (120 mL). The reaction was stirred for 30 minutes the Ecosorb 402-LM (200 mL) was added and the reaction was stirred for 5 minutes then filtered through Celite> The cake was rinsed with ethyl acetate (200 mL). Solvent was removed from the filtrate in vacuo and the resulting light yellow oil was pumped down to give the title compound (13.6 g, 85%).

EXAMPLE 3 morpholine hydrazone of compound (II)

Dimethyl-1,3,5-trioxepane-6,7-dicarboxylic acid (15 g, 68.1 mmol) was dissolved in toluene (200 mL) and cooled to −62° C. DIBAL-H (1.5M toluene, 100 mL) was added over 20 minutes then the reaction was stirred for 2 hours at −62° C. Methanol (6.5 mL, 160 mmol) was added slowly then the reaction was warmed to 0° C. over 90 minutes. 4-Aminomorpholine (14,4 mL, 150 mmol) was added and the reaction was stirred for 30 minutes. EtOAc (300 mL), Ecosorb and Celite were added and the reaction was warmed to room temperature. After 15 minutes of stirring the reaction was filtered and the filtrate was washed with brine (150 mL), and water (2×150 mL). The organic layer was dried ($MgSO_4$) and concentrated in vacuo to give 16.73 g (75%) of the title compound as a viscous, light yellow oil.

EXAMPLE 4 aminopiperazine hydrazine of compound (III)

Part A.

Preparation of benzyllithium. Tribenzyltin chloride (5.5 g, 12.8 mmol) was dissolved in toluene (200 mL) and degassed three times with nitrogen and house vacuum. The solution was cooled to 0° C. then methyllithium (1.4M pentane, 36.1 mL) was added over 5 minutes and the reaction became yellow. The solution was warmed to room temperature and stirred for two hours then cooled to −15° C.

Part B. Hydrazine formation. Hydrazone (5.7 g, 16.1 mmol) dissolved in toluene (60 mL) [prepared in previous example] was added to the −15° C. benzyllitium and stirred for 15 minutes. The reaction was warmed to 10° C. for one hour then water (50 mL) was added and the layers were separated. The organic layer was washed with brine and dried on $MgSO_4$ then stripped to give yellow viscous oil (8.8 g, 100%) containing some toluene.

EXAMPLE 5

Compound III, wherein $R^1$ and $R^2$ are methyl and $R^7$ is phenyl

Phenyllithium in diethyl ether and cyclohexane (1.8M, 5.0 mL) was added to toluene (15 mL) at −15 ° C. To this solution was added tetrahydrofuran (3 mL) followed by tetramethylhydrazone-1,3,5-trioxepane-6,7-dicarboxyaldehyde (1 g, 4.1 mmol). The reaction was stirred at −10 ° C. for one hour the warmed to room temperature for one hour. The reaction was washed with water (15 mL) then brine (15 mL). The organic fraction was dried on magnesium sulfate (2 g) and purified by column chromatography (methanol/methylene chloride, 1/99) to give the product (320 mg, 20%) as an amber oil.

EXAMPLE 6 morpholine hydrazine of compound (III)

Benzyllithium was prepared from tribenzyltin chloride as in Example 4 (Part A.). To the −15° C. solution of benzyllithium was added morpholine hydrazone (5.0 g, 15.2 mmol) in toluene (80 mL) and the reaction was stirred at room temperature overnight. The reaction was cooled to 0° C. and quenched with 15% NaCl aq. (200 mL). The layers were separated and the organic layer was washed with brine (100 mL) and water (100 mL). The combined aqueous fractions were back extracted with toluene (100 mL) and then EtOAc (100 mL). The combined organic layers were dried (MgSO₄) and concentrated in vacuo and purified by column chromatography (4:1 EtOAc:heptane to EtOAc) to give the title compound as a white foam (1.61 g, 21%).

EXAMPLE 7

[6α(S*),7β(S*)]-α,α'-bis(phenylmethyl)-1,3,5-trioxepane-6,7-dimethanamine dibenzenesulfonate Step (4).

1,1'-[1,3,5-trioxepane-6,7-diylbis(phenylethylidene)]bis[2,2-dimethylhydrazine](20 g, 84.83% wt) was mixed with 200 mL methanol and 10.9 g wet Raney nickel catalyst into a Parr pressure reactor. The system was inert with argon and then pressurized with hydrogen. The reaction mixture was stirred rapidly and maintianed at 100° C. and 180–250 psi hydrogen for 22 hours. The reaction was cooled down, inert, and sampled to show complete reaction. The catalyst was removed by filtration and the filtrate was concentrated to 14.2 g oil. This oil was assayed to be 80.9% wt [6α(S*),7β(S*)]-α,α'-bis(phenylmethyl)-1,3,5-trioxepane-6,7-dimethanamine (84.7% yield to this point). An 11.8 g (<33 mmol [6α(S*),7β(S*)]-α,α'-bis(phenylmethyl)-1,3,5-trioxepane-6,7-dimethanamine) portion of the oil was dissolved in 59 mL THF and stirred at. 50° C. A solution of 11.1 g benzenesulfonic acid (98%, 69 mmol) in 24 mL THF was added dropwise in 15 minutes. The slurry was stirred 15 minutes at ambient temperature, then chilled to −8° C. for 45 minutes. The solid was filtered and rinsed with cold THF. The wet cake was dried by pulling nitrogen through it overnight to give 16.7 g white solid assayed to be 91.5% wt [6α(S*),7β(S*)]-α,α'-bis(phenylmethyl)-1,3,5-trioxepane-6,7-dimethanamine dibenzenesulfonate. The yield from 1,1'-[1,3,5-trioxepane-6,7-diylbis(phenylethylidene)]bis[2,2-dimethylhydrazine] was 70.5%.

EXAMPLE 8

(5aα,6α,10β,10aα)hexahydro-6,10-bis(phenylmethyl)-8H-1,3,5-trioxepino[6,7-e][1,3]diazepin-8-one Step (5).

[6α(S*),7β(S*)]-α,α'-bis(phenylmethyl)-1,3,5-trioxepane-6,7-dimethanamine (100 g, 0.1375 mol) was suspended in acetonitrile (1 L) and triethylamine (21.1 mL, 0.1513 mmol) was added. The resulting solution was cooled to 5° C. and a solution of carbonyl diimidazole (11.15 g, 0.688 mmol) in acetonitrile (0.5 L) was added over 50 minutes. The reaction was then warmed to room temperature and held for one hour. Carbonyl diimidazole (5.6 g, 0.344 mmol) was added as a solid and the reaction stirred for one hour. Another charge of carbonyl diimidazole (5.6 g, 0.344 mmol) was added as a solid and the reaction stirred another hour. A final charge of solid carbonyl diimidazole (3.3 g, 0.206 mmol) was added and the reaction was stirred overnight. 4-Methyl-2-pentanone (1 L) and 1N hydrochloric acid (0.5 L) were added and the layers were separated. The organic layer was washed with additional 1N hydrochloric acid (0.5 L) and the layers separated. The combined aqueous layers were back extracted with 4-methyl-2-pentanone (2×0.3 L). The combined organic layers were reduced to 1.5 L and then washed first with brine (0.5 L) then with 8% sodium bicarbonate (0.5 L). The organic layer was reduced to 0.3 L then hexanes (1 L) were added. The resulting slurry was cooled in an ice bath for 1.5 h the filtered and rinsed with cold hexanes (100 mL). The white solid was dried under vacuum at 90° C. to give 46.66 g (83%), mp 125°–130° C.

What is claimed is:

1. The compounds of the formulae:

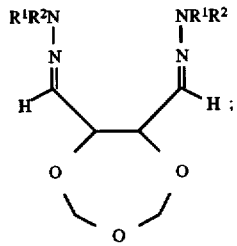

(II)

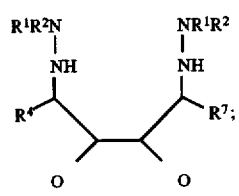

(III)

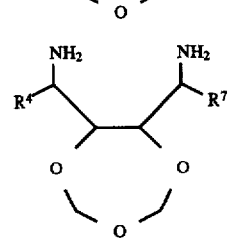

(IV)

wherein:

R¹ and R² are independently selected from the group: C₁-C₄ alkyl, acetyl, phenyl; or R¹ and R² may be taken together to form a ring such as triazole, 4-methylpiperazine, or morpholine;

R⁴ and R⁷ are independently selected from the group: hydrogen;
C₁-C₈ alkyl substituted with 0–3 R¹¹;
C₃-C₁₄ carbocyclic ring system substituted with 0–3 R¹¹ or 0–3 R¹²;
a 5- to 10-membered heterocyclic ring system containing 1 to 4 heteroatoms independently selected from oxygen, nitrogen or sulfur, said heterocyclic ring system being substituted with 0–2 R¹²;

R¹¹ and R¹¹ᴬ are independently selected at each occurrence from the group:
H, —CH₂NR¹³R¹⁴, —NR¹³R¹⁴, —OR¹³, —S(O)ₘR¹³, —NR¹⁴SO₂NR¹³R¹⁴, —NR¹⁴SO₂R¹³, —SO₂NR¹³R¹⁴, C₁-C₄ alkyl, C₂-C₄ alkenyl, C₃-C₆ cycloalkylmethyl, benzyl, phenethyl, phenoxy, benzyloxy, nitro, C₇-C₁₀ arylalkyl, boronic acid, C₃-C₆ cycloalkoxy, C₁-C₄ alkyl substituted with —NR¹³R¹⁴, C₁-C₄ hydroxyalkyl, methylenedioxy, ethylenedioxy, 2-(1-morpholino)ethoxy, azido;

C₃-C₁₀ cycloalkyl substituted with 0–2 R¹²;
C₁-C₄ alkyl substitued with 0–2 R¹²;
aryl(C₁-C₃ alkyl)-, substituted with 0–2 R¹²;
C₂-C₆ alkoxyalkyl-, substituted with 0–2 R¹²;
C₅-C₁₄ carbocyclic residue substituted with 0–3 R¹²;
a 5- to 10-membered heterocyclic ring system containing 1 to 4 heteroatoms independently selected from oxygen, nitrogen or sulfur, said heterocyclic ring system being substituted with 0–3 R¹²;

$R^{12}$, when a substituent on carbon, is independently selected at each occurrence from the group:

phenyl, benzyl, phenethyl, phenoxy, benzyloxy, nitro, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, methylenedioxy, ethylenedioxy, —$S(O)_mR^{13}$, —$SO_2NR^{13}R^{14}$, —$NHSO_2R^{14}$, 2-(1-morpholino) ethoxy; or a 5- or 6-membered heterocyclic ring containing from 1 to 4 heteroatoms independently selected from oxygen, nitrogen or sulfur;

or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy; or —$NR^{13}R^{14}$; or when $R^{12}$ is attached to sulfur it may be =O;

$R^{12}$, when a substituent on nitrogen, is independently selected at each occurrence from the group:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group:

H;
phenyl substituted with 0–3 $R^{11A}$;
benzyl substituted with 0–3 $R^{11A}$;
$C_1$–$C_6$ alkyl substituted with 0–3 $R^{11A}$;
an amine protecting group when $R^{13}$ is bonded to N;
a hydroxy protecting group when $R^{13}$ is bonded to O;

$R^{14}$ is independently selected at each occurrence from the group: hydrogen, hydroxy, $C_1$–$C_6$ alkyl substituted with 0–3 groups selected from OH, $C_1$–$C_4$ alkoxy, $NH_2$, —$NH(C_1$–$C_4$ alkyl), $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$.

2. A compound of claim 1 wherein:

$R^4$ and $R^7$ are independently selected at each occurrence from the group:
hydrogen;
$C_1$–$C_8$ alkyl substituted with 0–3 $R^{11}$;
$C_3$–$C_8$ cycloalkyl substituted with 0–3 $R^{11}$;
$C_6$–$C_{10}$ bicycloalkyl substituted with 0–3 $R^{11}$;
aryl substituted with 0–3 $R^{12}$;
a $C_6$–$C_{14}$ partially unsaturated carbocyclic residue substituted with 0–3 $R^{12}$;
a 5- to 6-membered heterocyclic ring system containing 1 to 3 heteroatoms independently selected from oxygen, nitrogen or sulfur, said heterocyclic ring system being substituted with 0–2 $R^{12}$.

3. A compound of claim 1 wherein:

$R^4$ and $R^7$ are independently selected at each occurrence from the group:

hydrogen;
$C_1$–$C_4$ alkyl substituted with 0–3 $R^{11}$;

$R^{11}$ is independently selected at each occurrence from the group:

H, cyano, —$CH_2NR^{13}R^{14}$, —$NR^{13}R^{14}$, —$OR^{13}$, $C_2$–$C_4$ alkoxyalkyl, —$S(O)_mR^{13}$, $C_1$–$C_4$ alkyl, $C_3$–$C_{10}$ cycloalkyl;

a $C_5$–$C_{14}$ saturated or partially unsaturated carbocyclic residue substituted with 0–3 $R^{12}$;
aryl($C_1$–$C_3$ alkyl)-substituted with 0–2 $R^{12}$;
aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$ when a substituent on carbon, is independently selected at each occurrence from the group:

phenyl, benzyl, phenethyl, phenoxy, benzyloxy, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, 2-(1-morpholino) ethoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, —$S(O)_mR^{13}$, —$SO_2NR^{13}R^{14}$; or a 5- or 6-membered heterocyclic ring containing from 1 to 4 heteroatoms independently selected from oxygen, nitrogen or sulfur;

or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —$NR^{13}R^{14}$; or when $R^{12}$ is attached to sulfur it may be =O;

$R^{12}$, when a substituent on nitrogen, is independently selected at each occurrence from the group:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl;

$R^{13}$ is independently selected at each occurrence from the group: H, $C_1$–$C_6$ alkyl, $C_3$–$C_6$ alkoxyalkyl, phenyl, or benzyl;

$R^{14}$ is independently selected at each occurrence from the group: OH, H, $CF_3$, $C_1$–$C_4$ alkyl, $C_1$–$C_4$ alkoxy, $NH_2$, phenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—.

4. The compounds of claim 1 wherein:

$R^4$ and $R^7$ are independently selected at each occurrence from the group: benzyl, fluorobenzyl, pyrrolylmethyl, methoxybenzyl, isobutyl, nitrobenzyl, aminobenzyl, thienylmethyl, hydroxybenzyl, pyridylmethyl, or naphthylmethyl;

$R^4$ and $R^7$ are both benzyl, isobutyl, 4-nitrobenzyl, 4-fluorobenzyl, 3-methoxybenzyl, 4-methoxybenzyl, 4-hydroxybenzyl, 4-(2-hydroxyethoxy)benzyl, 4-(2-morpholinylethoxy)benzyl, 3-($H_2NC$(=O)$CH_2O$) benzyl, 3,4-difluorobenzyl, 2-naphthylmethyl, 2-thienylmethyl, 4-methylthiobenzyl, isopropyl, or 4-pyridylmethyl;

$R^4$ is 4-nitrobenzyl and $R^7$ is 2-nitrobenzyl; and $R^4$ is 4-aminobenzyl and $R^7$ is 2-aminobenzyl.

* * * * *